(12) United States Patent
Yoon

(10) Patent No.: US 6,524,344 B2
(45) Date of Patent: Feb. 25, 2003

(54) CEMENT JACKET FOR A CEMENTED ARTIFICIAL JOINT STEM AND ARTIFICIAL JOINT HAVING THE CEMENT JACKET

(75) Inventor: Yong-San Yoon, Taejon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/779,304

(22) Filed: Feb. 8, 2001

(65) Prior Publication Data

US 2001/0014828 A1 Aug. 16, 2001

(30) Foreign Application Priority Data

Feb. 16, 2000 (KR) .......................................... 2000-7362

(51) Int. Cl.⁷ ................................ A61F 2/30; A61F 2/36
(52) U.S. Cl. ................................ 623/23.46; 623/23.19; 623/23.21; 623/23.22; 623/23.34
(58) Field of Search .......................... 623/23.21, 23.22, 623/23.23, 23.25, 23.46, 22.11, 23.29, 23.31, 23.15, 23.19, 23.2, 23.26, 23.44, 23.45, 23.34, 23.35, 23.36, 23.37, 23.62; 606/92, 93, 94, 95

(56) References Cited

U.S. PATENT DOCUMENTS

| | | | | |
|---|---|---|---|---|
| 4,064,567 A | * | 12/1977 | Burstein et al. ............... | 3/1.91 |
| 4,065,817 A | * | 1/1978 | Branemark et al. ........... | 3/1.91 |
| 4,549,319 A | * | 10/1985 | Meyer ...................... | 623/22.25 |
| 4,619,659 A | * | 10/1986 | Witzel ......................... | 623/23 |
| 4,718,916 A | * | 1/1988 | Morscher ...................... | 623/23 |
| 4,728,335 A | * | 3/1988 | Jurgutis ..................... | 623/23.26 |
| 5,180,395 A | * | 1/1993 | Klaue ........................ | 623/23 |
| 5,443,523 A | * | 8/1995 | Mikhail ...................... | 623/23 |
| 5,702,443 A | | 12/1997 | Bränemark | |
| 5,702,445 A | | 12/1997 | Bränemark | |
| 5,871,549 A | * | 2/1999 | Jayashankar et al. ......... | 623/22 |
| 5,935,172 A | * | 8/1999 | Ochoa et al. ................. | 623/18 |
| 6,123,730 A | * | 9/2000 | Ling ...................... | 623/23.25 |
| 6,168,626 B1 | | 1/2001 | Hyon et al. | |
| 6,214,053 B1 | * | 4/2001 | Ling et al. ............... | 623/23.11 |
| 6,217,620 B1 | * | 4/2001 | Park ....................... | 623/23.26 |
| 6,293,971 B1 | * | 9/2001 | Nelson et al. ........... | 623/23.63 |

* cited by examiner

Primary Examiner—Bruce Snow
Assistant Examiner—Cheryl J Miller
(74) Attorney, Agent, or Firm—Richard M. Goldberg

(57) ABSTRACT

A cement jacket for a cemented artificial joint stem, the cement jacket including a main body with a hollow interior and an open upper end for receiving and enclosing at least a part of a stem of an artificial joint, the cement jacket being shaped and adapted for longitudinal insertion in an opening formed in a bone canal of a human body, the cement jacket being made of cement and reinforced by imbedded wire or fiber and having an inner surface coated with a plastic film having a high resistance to abrasion, and the outer surface of the cement jacket is formed with discharging paths in the longitudinal direction so that excessive cement paste previously poured into the bone canal for the surgical purpose can be easily discharged upward at the time of inserting the jacket.

8 Claims, 4 Drawing Sheets

CEMENT JACKET FOR A CEMENTED ARTIFICIAL JOINT STEM AND ARTIFICIAL JOINT HAVING THE CEMENT JACKET

BACKGROUND OF THE INVENTION

1. Field of the Invention

The present invention relates to a cement jacket for a cemented artificial joint stem, and particularly to a cement jacket for a cemented artificial joint stem, with jacket secured to the bone in such a manner that the artificial joint stem can slide relative to the bone and said jacket enclosing the surface of the artificial joint stem. The invention also relates to an artificial joint having the artificial joint stem enclosed in the cement jacket.

2. Description of the Prior Art

Generally, an artificial hip joint, for example, consists of an acetabular part and a femoral or thigh bone part, wherein the acetabular and femoral parts are made of either metal, plastic, or ceramic, independently.

The human femur is formed of the cortical bone containing soft marrow. Therefore, in order to insert an artificial joint into the human body, operation is conducted in such a way that the bone canal is reamed out, the stem of artificial joint is inserted and finally anchorage is conducted by using cement(cemented) or mechanical tight fit (cementless).

In the cemented system, the cement used for fixing the artificial joint stem to the human femur has no chemical bonding or adhesive strength but only physical binding strength.

The art for surgical operation based on the artificial joint as described above is disclosed in the Korean patent publication 1814/1985 to the present applicants as the patentee, titled "Torsion resistant artificial hip joint".

Referring to FIG. 1, the art is briefly reviewed.

The artificial joint 1 is integrally composed of a head 2, neck 3, collar 4 and stem 5, starting with the top. The leading end of the collar 4 is curved to be secured tightly in the inner top edge of the cortex of the femur. The stem 5 is in a curved column with the top cross section resembling an ellipse which gradually varies to a circle at the bottom. Such a shape of the stem 5 is intended for protection from rotating due to the compressive force applied vertically from the top of the joint and the lateral force applied in the perpendicular direction to the stem of the joint.

Further, on the upper external surface of such a stem 5 a blade 7 with an appropriate thickness is provided protrusively in the longitudinal direction to prevent the joint from turning in the femur even in the case of a torque generated in an arbitrary direction after a surgery, wherein a fixing hole 8 is formed in the center of the blade 7.

On the inward side of the blade 7, the stem 5 is formed with a number of lateral grooves at certain longitudinal intervals, in which grooves iron wires 9 in chain form are inserted in a manner of wrapping the stem. On the surface of the stem 5 including the surface with chain-like wires 9, cement 6 is coated to a certain thickness. Such a process of pre-coating with cement 6 is to facilitate adhesion with the cement used in the surgical operation and to reduce the heat generated during the curing period through the reduced use of cement.

In order to introduce such an artificial joint in a human long bone, reaming is carried out at the bone canal beforehand so that the artificial joint 1 may be inserted with the stem 5, after appropriate amount of cement is injected thereto. Subsequently, the stem 5 is inserted in the cement-injected area, so that this cement may adhere with the pre-coated cement layer 6 on the surface of the stem 5, with the result that the stem 5 can be firmly secured in the femur.

As hinted before, while the artificial joint implanted in a human body is used, the cement layer used for fixing the stem of the artificial joint frequently falls apart from the femur, causing a gap between the femur and the stem.

In addition, the stem of the artificial joint according to a conventional art tends to be adhered with the cement layer formed during an operation or manufacturing. Such cement layer can lead to the formation of the fibrous tissue membrane on the femur due to the action of the shear force at the boundary between the femur and the stem, initiated by the vertical force acting at the head of the stem, to thereby form an effective joint space. Then the wear particles produced by the sliding action between the acetabular cup and the femoral head may penetrate into the gap or effective joint space formed between the bone and the stem and accelerate osteolysis of the bone as a serious drawback.

Further, for an artificial joint according to the conventional art, a substantial part of the vertical force is transferred to the lower side and therefore the upper side of a femur is depleted of stress and so associated with the defect of weakening due to stress shielding.

Moreover, the cement layer formed during an operation for a cemented implant such as an Exeter stem, exhibits a poor mechanical property (for example, the tensile strength amounting to less than a half of the normal value) and so has the risk of easy breakage. Additionally, a risk of mutual contact of the stem and the bone exists due to the difficulty in securing a uniform thickness of cement, which may provide a passage of wear particles from the acetabulum cup into the femoral bone-cement interface and invoke osteolysis at the site. There is also a possibility of break at the tip portion of the stem, when the stem sinks under a vertical load.

SUMMARY OF THE INVENTION

Therefore, the present invention was created to resolve the problem with the conventional art as described above and the object of the present invention is to provide a cement jacket for a cemented artificial joint stem, wherein shear force negative to the service life of an artificial joint can be markedly reduced and stress shielding phenomena can also be markedly relieved, due to the construction of the jacket which can be fixed to the bone canal(for example, femoral canal) and can enclose the surface of the stem so as to allow for the cemented artificial joint stem to slide vertically relative to the bone, and wherein osteolysis of a bone due to the infiltration of wear particles can be minimized by suppressing the gap formation between the bone and the stem.

Further, another object of the present invention is to provide an artificial joint in which the stem is covered by a cement jacket for cemented artificial stem.

To achieve the above first object, there is provided, according to an aspect of the invention, a cement jacket for the cemented artificial joint stem for enclosing at least a part of the cemented artificial joint stem which is inserted longitudinally in the opening formed in the proximal end part of the femur of a human body.

Preferably, the cement jacket is made of cement.

Preferably it is also provided that the inner surface of said cement jacket is formed with a plastic film having a high resistance to abrasion.

Further, it is provided, the outer surface of said cement jacket is formed with discharging paths in the longitudinal direction, so that the cement poured in the bone canal previously for the surgical purpose can be easily discharged upward at the time of inserting the jacket as well as enhancing anchorage of the new cement mantle with the jacket.

To achieve the above-described second object of the invention, according to another aspect of the invention, there is provided an artificial joint with a cement jacket for the artificial joint stem, said artificial joint is integrally formed of a head, neck and stem so as to be inserted into an opening formed by digging out a part of the bone(femur) in a human body, wherein the cement jacket is so formed that it may enclose at least a part of said stem and the stem may slide vertically in a longitudinal direction and wherein the lower end part of the jacket has a surplus empty space to allow for the stem to slide downward.

In the case of using an artificial joint equipped with a cement jacket for the stem according to the invention, predominantly a compressive force comes into action between the bone and the cement jacket to suppress the formation of fibrous tissue membrane, to activate or fortify the bone, and to reduce the shear stress detrimental to the bone at the interface between the bone and the cement jacket and turn the stress into a compressive force beneficial to the bone. Such enhanced compressive force strengthens the bone and acts to minimize the osteolysis of bone due to the infiltration of wear particles by deterring the formation of gap between the bone and the cement mantle. Also, it is known that the shear stress at the cement-bone interface invokes micromotion at that interface and eventually will develop soft-tissue membrane at that interface, which is detrimental to the fixation of the stem. The said jacket definitely will reduce this kind of undesirable shear stress at the bone-cement interface by increasing the compressive stress which is beneficial as aforementioned.

Further, in the case of using an artificial joint equipped with a cement jacket for a stem according to the invention, the vertical force is transferred into the bone hoop stress, which induces tensile stress large enough to physiologically activate the femur (Wolfe's law) even at the proximal region of the femur bone, alleviating the phenomena of stress shielding drastically.

Furthermore, the cement jacket for an artificial joint stem according to the invention has the advantage that the generation of wear particles from frictional contact with the stem can be minimized by coating a film of plastic resistant to wearing-out, preferably polyethylene film on the inner surface of the jacket.

Still further, the cement jacket according to the invention has the advantage that direct contact between the femur and the stem is prevented by providing a strong and uniform cement layer and breakage of a jacket due to the vertical sag of a stem is prevented by securing a space between the end of the jacket and the end of the stem.

DESCRIPTION OF A PREFERRED EMBODIMENT

A preferred embodiment of a cement jacket for a cemented artificial joint stem and an artificial joint equipped with that cemented jacket will be described in detail below by referring to accompanying drawings.

Figure 1:
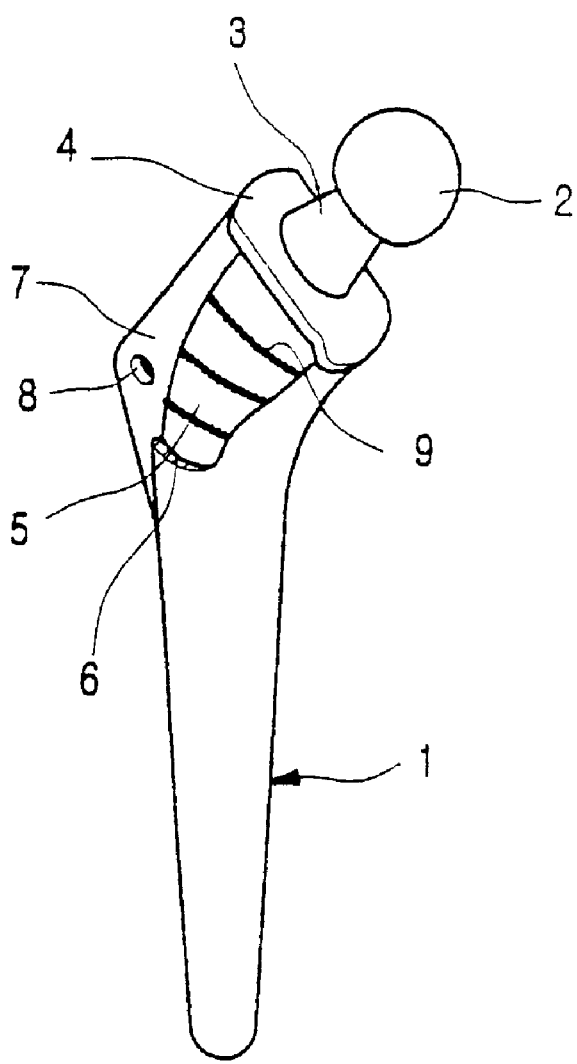
FIG. 1 shows the perspective view of an artificial joint according to a conventional art to illustrate constituting components.
Figure 2:
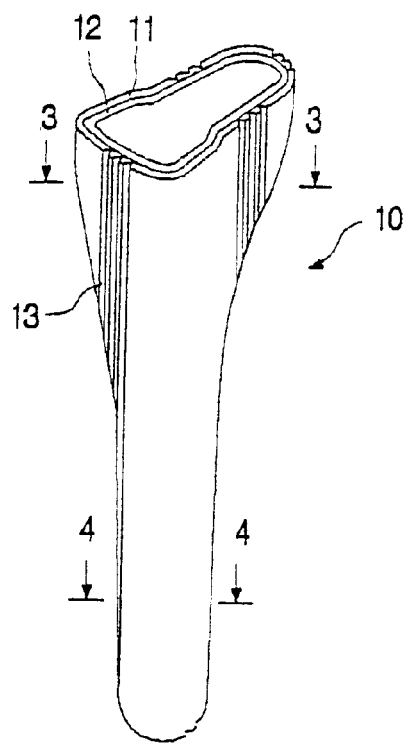
FIG. 2 shows the perspective view of a cement jacket for a cemented artificial joint stem according to an embodiment of the invention to illustrate constituting components.
Figure 3:
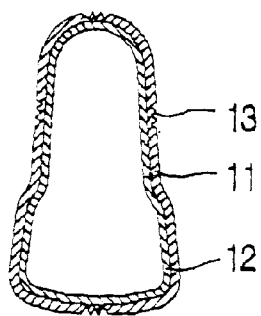
FIG. 3 shows the cross section along the line 3—3 of the cement jacket for the cemented artificial joint stem shown in FIG. 2.
Figure 4:
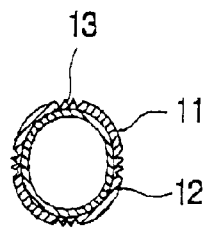
FIG. 4 shows the cross section along the line 4—4 of the cement jacket for the cemented artificial joint stem shown in FIG. 2.

As can be seen in FIGS. 2 to 4, the cement jacket 10 for cemented artificial joint stem according to a preferred embodiment of the invention is in the form adapted for enclosing the stem when the stem is inserted, or in the form of a bag, preferably with tight fit between the jacket and the stem, so that small vertical sliding movement of the stem may be allowed while lateral motion of the stem within the jacket 10 is prevented.

The cement jacket 10 is formed a little longer than the stem so that a predetermined space between the lower end of the stem and the lower end of the jacket remains to prevent the lower tip of the stem from touching the lower end of the jacket when the tip is placed in the jacket. The formation of such a prescribed space is to prevent a damage on the cement jacket 10, if the stem sinks downward.

Further, the cement jacket 10 is generally made of the same cement as that used for fixing the stem of artificial joint to the bone, wherein the inside surface of the cement jacket to be in contact with the stem is often formed with an ultrahigh molecular weight polyethylene or equivalent plastic layer 12 to minimize the abrasion owing to the vertical sliding of the stem with the cement jacket. That is, the cement jacket 10 may be made of all cement or all plastic or otherwise the cement jacket 10 may be composed of an external cement layer 11 made of cement and an internal plastic layer 12 made of plastic. Further, the inside of the cement jacket 10 may be reinforced with wires or fibers. The respective thickness of the cement layer 11 and the plastic layer 12 constituting the cement jacket may be varied as required.

The outer surface of a cement jacket 10 is formed with discharging paths 13, through which the cement already injected in the bone canal may be discharged up along the surface of the cement jacket 10 as the cement jacket 10 with the stem is being inserted into the bone canal in a human body. The discharging paths 13 in the form of saw-toothed grooves are laid parallel in the longitudinal direction of the cement jacket 10. In the illustrated embodiment shown in FIG. 2, there are 4 sets of discharging paths each consisting of certain ridges and valleys and distributed at finite intervals around the circumference of the cement jacket. The discharging paths 13 can be formed all over the surface of the cement jacket 10 and more than or less than 4 sets may be employed. Formation of such discharging paths 13 has the effect of increasing the area of exposed surface for the cement jacket 10, which contributes to facilitate the discharge of excessive cement paste during operation and to ensure the enhanced connecting strength between the operation-site cured cement mantle and the jacket.

Now, the procedure of inserting an artificial joint by using the cement jacket so constructed according to the invention will be described.

Figure 5:
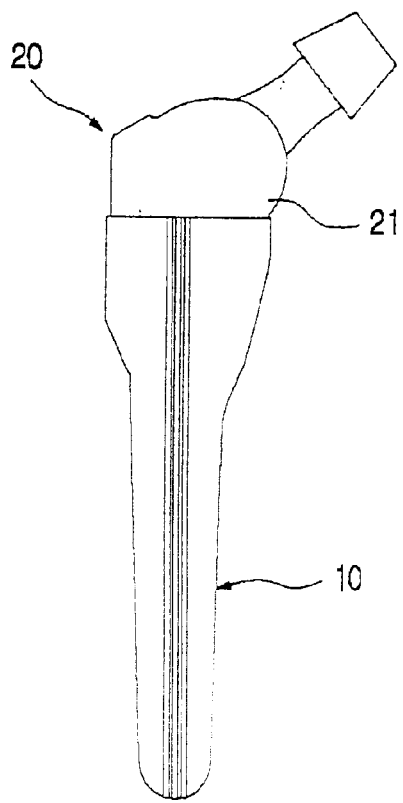
FIG. 5 shows a cemented artificial joint stem as inserted in the jacket shown in FIG. 2.

As can be seen from FIG. 5, the stem 21 of a conventional artificial joint 20, the surface of which is polished, is first inserted into a cement jacket 10 according to the invention. Then, a prescribed spacing between the lower end of stem 21 and the lower end of the cement jacket is formed, so that the jacket can slide down relative to the jacket, as mentioned earlier.

Figure 6:
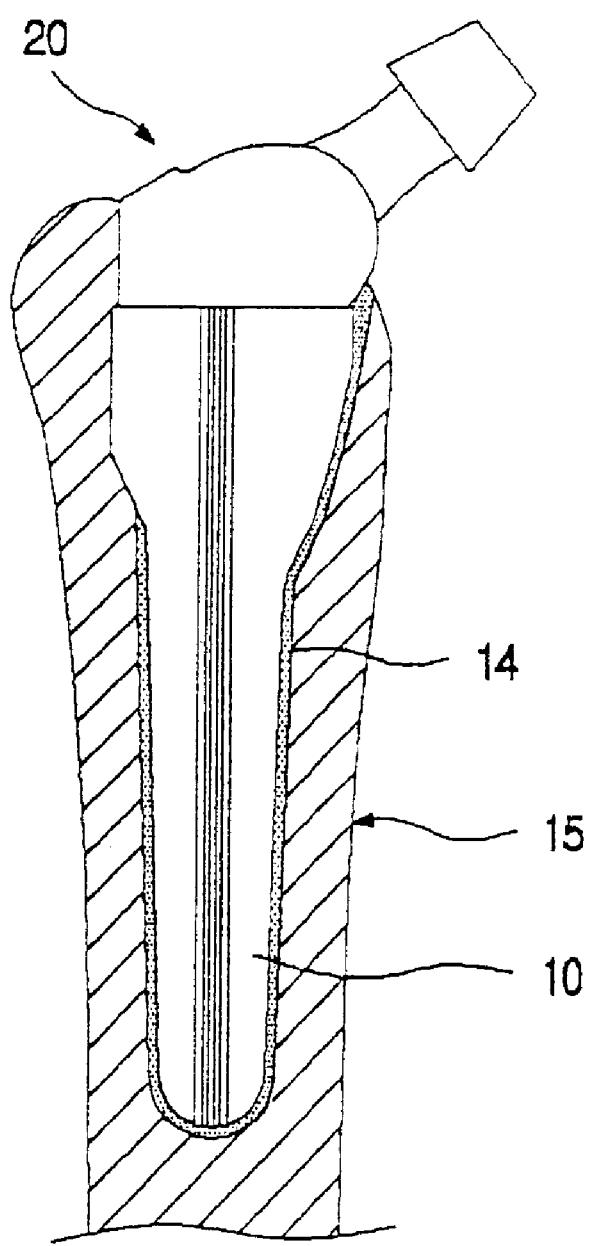
FIG. 6 shows an artificial joint shown in FIG. 5 as inserted into the bone(for example, femur) of a human body.

Now, the artificial joint 20, wherein the cement jacket 10 is placed around a stem 21, is to be inserted into the bone canal in human body. To that end, bone canal is first enlarged within the bone 15 to form an opening and an appropriate amount of cement paste 14 is poured in there, so that a cement jacket 10 in which the stem 21 of artificial joint 20 is placed may be inserted, as seen in FIG. 6. Next, the cement jacket 10 is inserted in the area where the cement paste 14 for the anchorage with the bone is poured into the bone canal during operation, so that excessive cement paste 14 is discharged along the discharging paths 13 formed on the surface of the cement jacket 10, resulting in firm anchoring of the stem 21 at the proper position and orientation inside the bone canal. Consequently, the bone 15 and the cement jacket 10 are rigidly anchored, while the stem 21 can slide up or down in relation to the jacket 10.

The cement jacket according to the present invention can be applied to all kinds of artificial joints including the hip joint, knee joint, shoulder joint and the like.

It is to be understood that, while the invention was described only with respect to a preferred embodiment of a cement jacket for a cemented artificial joint stem and an artificial joint having the same jacket, the invention is never restricted to that embodiment and a variety of modifications and alterations would be possible to a man skilled in the art by referring to the description or drawings presented here and within the spirit of the invention and thus those modifications or alterations are to fall within the scope of the invention, which scope should be limited only by the attached claims.

What is claimed is:

1. A cement jacket for an artificial joint stem, the cement jacket comprising:
   a hollow body made of cement and adapted to receive and encompass at least a part of a stem of an artificial joint therein,
   a closed lower end forming one end of the hollow body, and
   an open upper end forming an opposite end of the hollow body,
   a plastic layer having a high resistance to abrasion which coats an inner surface of the hollow body, and
   discharging paths having a saw-tooth shape in a transverse direction and extending in a longitudinal direction on and formed on an outer surface of the hollow body so that cement previously poured in a bone canal for a surgical purpose can be easily discharged upward at a time of inserting the cement jacket as well as enhancing anchorage of a new cement mantle with the cement jacket.

2. The cement jacket according to claim 1, wherein an inner surface of said cement jacket is reinforced with wires.

3. The cement jacket according to claim 1, wherein an inner surface of said cement jacket is reinforced with fibers.

4. The cement jacket according to claim 1, wherein the discharging paths on the outer surface of the cement jacket are cut into the outer surface so as not to protrude outward from the outer surface of the cement jacket.

5. An artificial joint comprising:
   an artificial joint stem which is integrally formed of a head, neck and stem portion, and
   a cement jacket comprising:
   the cement jacket comprising:
   a hollow body made of cement and adapted to receive and encompass at least a part of a stem of an artificial joint therein,
   a closed lower end forming one end of the hollow body, and
   an open upper end forming an opposite end of the hollow body,
   a plastic layer having a high resistance to abrasion which coats an inner surface of the hollow body, and
   discharging paths having a saw-tooth shape in a transverse direction and extending in a longitudinal direction on and formed on an outer surface of the hollow body so that cement previously poured in a bone canal for a surgical purpose can be easily discharged upward at a time of inserting the cement jacket as well as enhancing anchorage of a new cement mantle with the cement jacket.

6. The artificial joint according to claim 5, wherein the discharging paths on the outer surface of the cement jacket are cut into the outer surface so as not to protrude outward from the outer surface of the cement jacket.

7. The artificial joint according to claim 5, wherein the stem is freely slidable inside the cement jacket.

8. The artificial joint according to claim 5, wherein the cement jacket is firmly fixed in the bone canal as the poured cement contacts all of the surfaces of the discharging paths, which functions to increase an effective outer surface of the cement jacket.

* * * * *